United States Patent [19]

Marshall et al.

[11] Patent Number: 4,933,365
[45] Date of Patent: Jun. 12, 1990

[54] PHOSPHOLIPASE A2 INHIBITORS

[75] Inventors: Lisa A. Marshall, Fort Washington, Pa.; Kurt E. Steiner, Lawrenceville, N.J.; Guy A. Schiehser, Yardley, Pa.

[73] Assignee: American Home Products Corporation, New York, N.Y.

[21] Appl. No.: 301,937

[22] Filed: Jan. 25, 1989

[51] Int. Cl.$^5$ ............................................. A61K 31/335
[52] U.S. Cl. .................................................... 514/475
[58] Field of Search ......................................... 514/475

[56] References Cited

U.S. PATENT DOCUMENTS 4,788,304 11/1988 Marshall et al. ..................... 549/549
4,788,306 11/1988 Schiehser et al. .................... 549/549

Primary Examiner—Jerome D. Goldberg
Attorney, Agent, or Firm—George Tarnowski

[57] ABSTRACT

There is disclosed a method for the treatment of immunoinflammatory conditions, such as allergy, anaphylaxis, asthma and inflammation in mammals which comprises administering to a mammal so afflicated an effective amount of a compound having the formula:

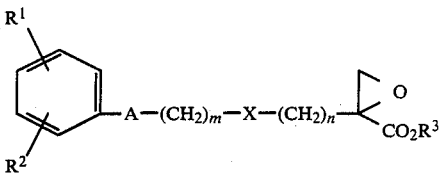

wherein
$R^1$ and $R^2$ are each, independently, hydrogen, hydroxy, lower alkyl, lower alkoxy, haloloweralkyl, haloloweralkyl sulfonyl, halo or nitro;
$R^3$ is hydrogen, lower alkyl, or aryl of 7–12 carbon atoms;
X is

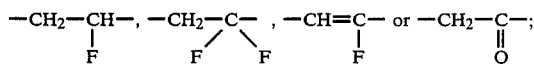

A is —$CH_2$—, —O— or —S—;
m is 0–8;
n is 0–7, with the proviso that $m+n \leq 8$;
or a pharmacologically acceptable salt thereof.

9 Claims, No Drawings

PHOSPHOLIPASE A2 INHIBITORS

The subject matter claimed in this application is discloses in related U.S. Pat. No. 4,788,304, issued November 29, 1988, to Lisa A. Marshall, Kurt E. Steiner and Guy A. Schiehser.

The present invention is directed to a method for using glycidic esters s anti-inflammatory agents.

It is now well-established that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. It is now known that prostaglandins arise from the endoperoxides $PGG_2$ and $PGH_2$ by the cyclooxygenase pathway of arachidonic acid metabolism. These endoperoxides are also the precursors of the thromboxanes (Tx) $A_2$ and $B_2$. $TxA_2$ is a vasoconstrictor which stimulates platelet aggregation. In the normal situation, the vasoconstrictive and platelet aggregating properties of the thromboxanes are balanced by another product arising from the endoperoxides in the cyclooxygenase pathway, prostacyclin ($PGI_2$), which is a vasodilator with platelet aggregation inhibitory activity. In the event prostacyclin synthesis is impaired and/or platelet activation is enhanced, then thrombosis and vasoconstriction is favored. The role of prostanoids in haemostasis and thrombosis are reviewed by R. J. Gryglewski, *CRC Crit. Rev. Biochem.*, 7, 291 (1980) and J. B. Smith, *Am. J. Pathol.*, 99, 743 (1980). Cyclooxygenase metabolites are known to participate directly in the inflammatory response [see Higgs et al., Annals of Clinical Research, 16, 287-299 (1984)]. This is through their vaso-depressor activities, participation in pain and fever augmentation of peptide mediator vascular permeability and edema forming properties. Finally, various aspects of cell mediated immunity are influenced by cyclooxygenase products.

The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Bach et al., *J. Immun.*, 215, 115-118 (1980); *Biochem. Biophys. Res. Commun.*, 93, 1121-1126 (1980)].

The significance of these leukotrienes is that a great deal of evidence is accumulating showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature*, 288, 484-486 (1980)], and another leukotriene, $LTB_4$, is a powerful chemotactic factor for leukocytes [see A. W. Ford-Hutchinson, *J. Roy. Soc. Med.*, 74, 831-833 (1981)]. The activity of leukotrienes and slow-reacting substances as mediators of imflammation and hypersensitivity is extensively reviewed in Bailey and Casey, *Ann. Reports Med. Chem.*, 17, 203-217 (1982).

Phospholipase $A_2$ ($PLA_2$) is the critical rate limiting enzyme in the arachidonic acid (AA) cascade since it is responsible for the hydrolysis of esterified AA from the C-2 position of membrane phospholipids. This reaction generates two products (1) free AA which is then available for subsequent metabolism by either the cyclooxygenase or lipoxygenase enzymes and (2) lysophospholipid. When alkyl-arachidonoyl-glycerophosphatidylcholine is acted upon by the $PLA_2$ the generation of platelet activating factor (PAF) is initiated: PAF is pro-inflammatory in its own right [see Wedmore et al., *Br. J. Pharmacol.*, 74, 916-917 (1981)]. In this regard it may be noted that the anti-inflammatory steroids are through to inhibit eicosanoid synthesis by inducing the synthesis of a $PLA_2$ inhibitory protein denominated macrocortin or lipomodulin [see Flower et al., *Nature, London*, 278, 456 (1979) and Hirata et al., *Proc. Natn. Acad. Sci. U.S.A.*, 77, 2533 (1980)].

As the initial step leading to subsequent conversion of AA to the various eicosanoids by the cyclooxygenase and lipoxygenase pathways, the $PLA_2$-mediated release of AA from membrane phospholipids is a critical event in attempting to deal with the various physiological manifestations which are based on the activity of the eicosanoids and/or PAF. Thus, while $PLA_2$ has been shown to be required for platelet aggregation [Pickett et al., *Biochem. J.*, 160, 405 (1976)], cardiac contraction and excitation [Geisler et al., *Pharm. Res. Commun.*, 9, 117 (1977)], as well as prostaglandin synthesis [Vogt, *Adv. Prostagl. Thromb. Res.*, 3, 89 (1978)], the inhibition of $PLA_2$ is indicated in the therapeutic treatment of both PAF induced or cyclooxygenase and/or lipoxygenase pathway product-mediated physiological conditions. Thus, $PLA_2$ inhibitors are a rational approach to the prevention, removal or amelioration of such conditions as allergy, anaphylaxis, asthma and inflammation.

The invention provides novel compounds of the formula

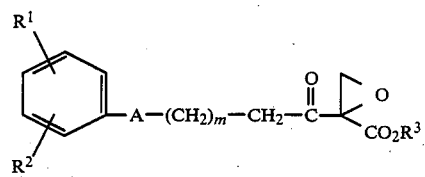

wherein $R^1$ and $R^2$ are each, independently, hydrogen, hydroxy, lower alkyl, lower alkoxy, haloloweralkyl, haloloweralkylsulfonyl, halo or nitro;

$R^3$ is hydrogen, lower alkyl or aryl of 6-10 carbon atoms;

A is $-CH_2-$, $-O-$ or $-S-$;

m is 0-8;

or a pharmacologically acceptable salt thereof.

The invention further provides a method for treating immuno-inflammatory conditions such as allergy, anaphylaxis, asthma and inflammation, in mammals, which comprises administering to a mammal so afflicted an effective amount of a compound having the formula

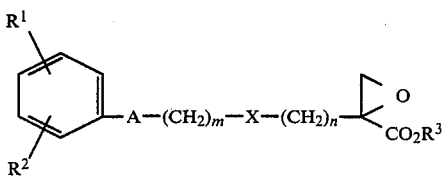

wherein $R^1$ and $R^2$ are each, independently, hydrogen, hydroxy, lower alkyl, lower alkoxy, haloloweralkyl, haloloweralkylsulfonyl, halo or nitro;

$R^3$ is hydrogen, lower alkyl or aryl of 6–10 carbon atoms;

X is

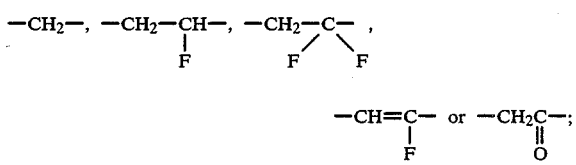

A is —$CH_2$—, —O— or —S—;
m is 0–8;
n is 0–7, with the proviso that $m+n \leq 8$;
or a pharmacologically acceptable salt thereof.

The compounds having the formula

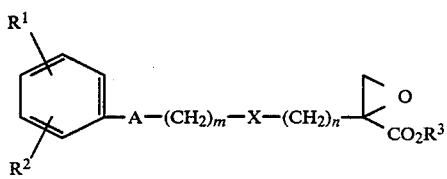

in which A is —$CH_2$ or —O— and X is —$CH_2$— and $m+n \leq 7$ are disclosed and claimed in U.S. Pat. Nos. 4,324,796 and 4,337,267, wherein they are disclosed to posssess hypoglycemic and hypoketonemic activity making them useful in the prophylaxis and treatment of disorders such as diabetes. Compounds of the formula in which A is —$CH_2$— or —O—, X is

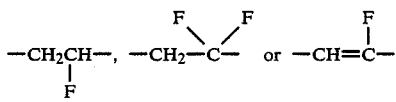

and $m+n \leq 8$ are disclosed and claimed in pending U.S. Pat. No. 4,788,306 in which they are disclosed to be fatty acid oxidation inhibitors and hypoglycemic agents. Compounds of the formula

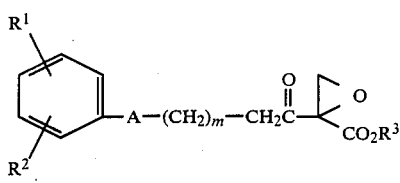

are likewise disclosed in U.S. Pat. No. 4,788,306, wherein they are used solely as intermediates for the preparation of final product compounds in which X is

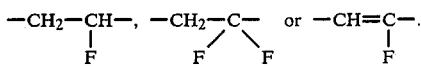

The terms "lower alkyl" and "lower alkoxy" refer to moieties having 1 to 6 carbon atoms in the carbon chain. The term "halo" refers to fluoro, bromo or chloro.

The pharmacologically acceptable salts include those of pharmacologically acceptable inorganic and organic acids, such as hydrochloric, hydrobromic, sulfuric, nitric, phosphoric, methanesulfonic, benzenesulfonic, acetic, citric, fumaric, malic, maleic, succinic and the like. Cations used for salt formation are those of the alkali metals, alkaline earth metals or earth metals, such as lithium, sodium, potassium, magnesium, calcium and aluminum. Cations corresponding to organic nitrogen bases, such as amines, aminoalkanols, aminosugars and basic amino acids may also be used. Exemplary of the latter are ethylenediamine, dimethylamine, diethylamine, morpholine, piperidine, piperazine, methylcyclohexylamine, benzylamine, ethanolamine, di- and triethanolamine, tris-(hydroxymethyl)aminomethane, glucamine, glucosamine, lysine, ornithine, arginine and the like.

The compounds within the scope of the invention by virtue of their configuration, exhibit stereoisomerism. Accordingly, the compounds of the invention include the diasteromers, enantiomorphos, racemates and mixtures thereof.

The compounds within the scope of the invention can be prepared by a variety of synthetic routes using conventional methods. According to one preparative scheme, for example, a suitable aldehyde is first reacted with methyl acrylate to give an allylic alcohol intermediate

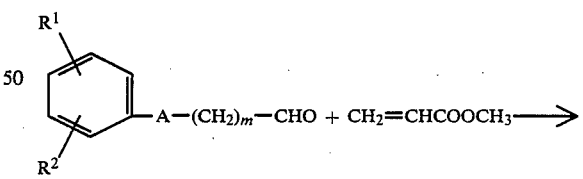

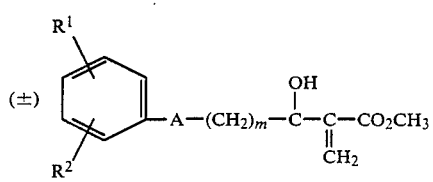

The allylic alcohol intermediate is then fluorinated to afford the allylic fluoride, which is then subjected to epoxidation to yield a mixture of two diasteromeric fluoroepoxides, which can be resolved by chromatographic separation

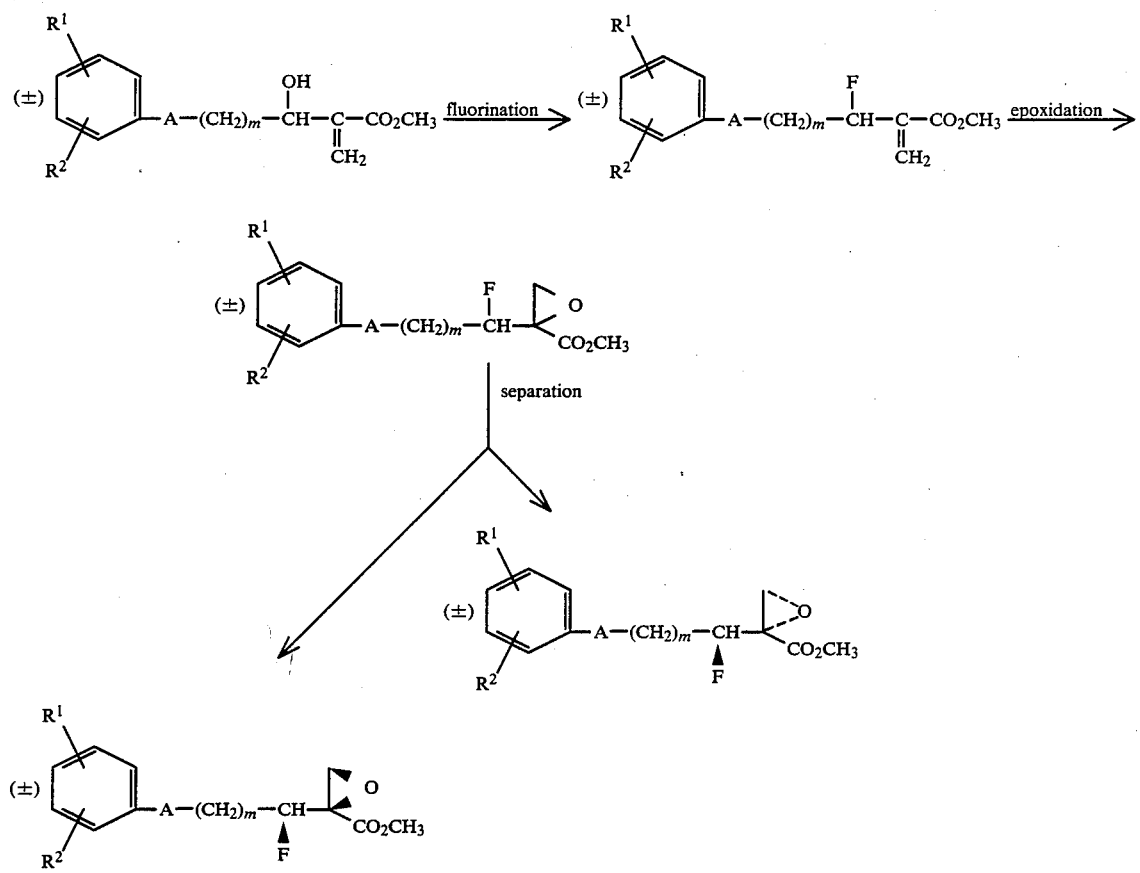

In an alternative scheme, the allylic alcohol may be first epoxidized to yield two diasteromeric epoxyalcohols. This mixture can then be fluorinated to give a mixture of final products which can be separated chromatographically.

It is also possible to prepare the diasteromeric epoxyalcohols, which may be first separated by preparative chromatography, and each diastereomer may then be individually converted to its corresponding fluoroepoxide.

The gen-difluoro- and vinyl fluoro- containing compounds can be prepared via the alternative scheme described above, as follows

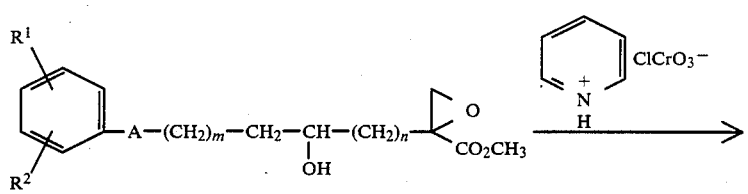

-continued

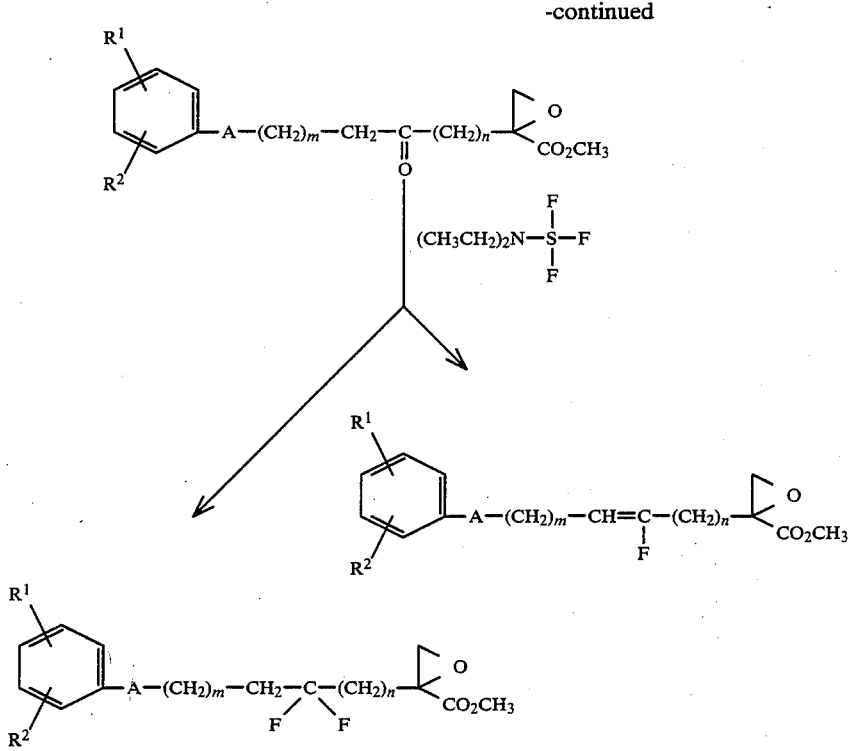

In the last step, the reaction of the ketone intermediate with the diethylaminosulfur trifluoride yields both the gem-difluoro- and vinyl fluoro-containing compounds, which are separated by preparative high pressure liquid chromatography. These ketone intermediates are themselves PLA$_2$ inhibitors and exhibit anti-inflammatory activity.

The compounds in which A is —CH$_2$— or —O— and X is —CH$_2$— can be prepared by the methods disclosed in U.S. Pat. Nos. 4,324,796 and 4,337,267. Those portions of these patents which disclose the methods of preparation and the representative examples thereof, to wit columns 7–26 and columns 9–22, respectively, are accordingly incorporated by reference herein.

The starting materials in the above preparative sequences are all commercially available or can be prepared by conventional methods as taught in the chemical literature.

The compounds of the invention, by virtue of their ability to inhibit activity of PLA$_2$ enzyme, are useful in the treatment of conditions mediated by products of the oxidation of arachidonic acid. Accordingly, the compounds are indicated in the prevention and treatment of such conditions as allergic rhinitis, allergic bronchial asthma and other naso-bronchial obstructive air-passageway conditions, other immediate hypersensitivity reactions, such as allergic conjunctivitis; and various inflammatory conditions such as those present in rheumatoid arthritis, osteoarthritis, tendinitis, bursitis, psoriasis (and related skin inflammation) and the like.

When the compounds within the scope of the invention are employed in the treatment of allergic airways disorders or in anti-inflammatory therapy, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, traga-canth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation of insufflation, the compoundsm may be formulated into an aqueous or partially aqueous solution, which can then be utilized in the form of an aerosol. The compounds may also be used topically and for this purpose they may be formulated in the form of dusting powders, creams or lotions in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The standard pharmacological procedures, which are described fully in the examples given hereafter, illustrate the ability of the compounds of the invention to inhibit the polymorphonuclear leukoxyte synthesis of the lipoxygenase product $LTB_4$ and the cyclooxygenase product $TxB_2$: the ability of the compounds to inhibit the activity of cell free human platelet $PLA_2$ enzyme in vitro; the in vivo ability of the compounds to inhibit bronchospasm induced by endogenous mediators of bronchoconstriction; the oral activity of the compounds in the $PLA_2$-induced cutaneous vascular permeability assay; and the anti-inflammatory activity of the compounds in the topical oxazolone contact hypersensitivity assay and in the murine ear edema and paw edema assays.

EXAMPLE 1

2-(1-Fluoro-5-phenylpentyl)-2-oxiranecarboxylic acid methyl ester

Method A (A) β-Hydroxy-α-methylenebenzeneheptanoic acid methyl ester (1) 5-phenyl-1-pentanal To a suspension of 20 g (93 mmol) of pyridinium chlorochromate in 300 ml of methylene chloride is added 9.9 g (60 mmol) of 5-phenyl-1-pentanol. The mixture is maintained at room temperature with vigorous stirring for 1.75 hours, diluted with ethyl ether and allowed to stand overnight. The mixture is filtered through Florisil with ethyl ether and rotoevaporated to give 8.4 g crude aldehyde which is used in the next reaction without further characterization.

(2) α-Hydroxy-α-methylenebenzeneheptanoic acid methyl ester

A mixture of 8.4 g (52 mmol) of 5-phenylpentanal, 8.95 g (104 mmol) of methyl acrylate and 200 mg of 1,4-diazabicyclo[2.2.2]octane is allowed to stand at room temperature for 120 hours.

Rotoevaporation gives an oil which is purified chromatographically (silica gel; hexane:ethyl ether (3:2)) to afford 3.1 g of the title compound: IR (neat) γ 3440, 1715 cm$^{-1}$; NMR (CDCl$_3$) δ 1.28-1.74 (6H, m), 2.61 (2H, t, J=8 Hz), 3.78 (3H, s), 4.39 (1H, t, J=6 Hz), 5.78 (1H, s), 7.19 (3H, m) and 7.28 (2H, m).

Analysis for: $C_{15}H_{20}O_3$; Calculated: C, 72.55; H, 8.12; Found C, 72.37; H, 8.09.

(B) 2-[1-Hydroxy-5-phenylpentyl]-2-oxiranecarboxylic acid methyl ester (isomer A)

2-[1-Hydroxy-5-phenylpentyl]-2-oxiranecarboxylic acid methyl ester (isomer B)

A solution of 11.2 g (45 mmol) of β-hydroxy-α-methylenebenzene-heptanoic acid methyl ester in 300 ml of 1,2-dichloroethane is treated with 200 mg of 4,4'-thiobis(6-t-butyl-m-cresol) and 24.5 g (138 mmol) of m-chloroperoxybenzoic acid. The mixture is heated to reflux under nitrogen for 26 hours.

The mixture is diluted with methylene chloride and is washed twice with aqueous saturated sodium sulfite. The combined methylene chloride layers are washed with aqueous sodium bicarbonate, dried over magnesium sulfate, filtered and rotoevaporated. The resultant oil is subjected to preparative HPLC (gradient elution - hexane:ethyl acetate (9:1) through ethyl acetate) to give 2.36 g of the more mobile isomer A (Rf 0.23 in hexane:ethyl ether (1:1)): IR (neat) γ 3520 (broad), 1730 cm$^{-1}$; NMR (CDCl$_3$) δ 1.42-1.84 (6H, m), 2.31 (1H, broad d, removed by D$_2$O exchange), 2.64 (2H, t, J=7 Hz), 3.01 (1H, d, J=6 Hz), 3.15 (1H, d, J=6 Hz), 3.80 (3H, s), 3.86 (1H, broad m), 7.21 (3H, m) and 7.30 (2H, m).

Analysis for: $C_{15}H_{20}O_4$; Calculated: C, 68.16; H, 7.63; Found: C, 67.98; H, 7.53.

and 0.68 g of the less mobile (Rf 0.12 in hexane:ethyl ether (1:1)) isomer B: IR (neat) γ 3480 (braod), 1728 cm$^{-1}$; NMR (CDCl$_3$) δ 1.30-1.80 (6H, m), 2.11 (1H, broad s, removed by D$_2$O exchange), 2.63 (2H, t, J=7 Hz), 2.98 (1H, d, J=6 Hz), 3.07 (1H, d, J=6 Hz), 3.76 (3H, s), 4.12 (1H, dd, J=3, 10 Hz), 7.20 (3H, m) and 7.30 (2H, m).

(C) 2-(1-Fluoro-5-phenylpentyl)-2-oxiranecarboxylic acid methyl ester (isomer A)

To a solution of 2.44 g (15 mmol; 2.01 ml) of diethylaminosulfur trifluoride in 50 ml of methylene chloride cooled to −78° C. under a nitrogen atmosphere is added dropwise a solution of 2.00 (7.6 mmol) of 2-[1-hydroxy-5-phenylpentyl]-2-oxiranecarboxylic acid methyl ester (isomer A) in 50 ml of methylene chloride over 30 minutes. The mixture is stirred at −78° C. for 90 minutes and then is allowed to come to room temperature. The mixture is stirred at room temperature for 1.5 hours, is quenched with a saturated aqueous solution of sodium bicarbonate and is extracted with ethyl ether. The combined ethereal extracts are dried over magnesium sulfate, filtered and rotoevaporated. The resulting oil is purified chromatographically (silica gel; hexane:ethyl acetate (9:1)) to give 1.19 g of the title compound (Rf 0.54 in hexane:ethyl ether (3:2)): IR (neat) γ 1750 cm$^{-1}$; NMR (CDCl$_3$) δ 1.40-1.96 (6H, m), 2.64 (2H, t, J=8 Hz), 3.07 (1H, dd, J=4, 6 Hz), 3.15 (1H, d, J=6 Hz), 3.79 (3H, s), 5.14 (1H, ddd, J$_{HF}$=49 Hz, J=10, 3 Hz), 7.21 (2H, d, J=8 Hz) and 7.31 (2H, d, J=8 Hz).

Analysis for: $C_{15}H_{19}FO_3$; Calculated: C, 67.67; H, 7.14; Found: C, 67.73; H, 7.30.

Method B (A) β-Fluoro-α-methylenebenzeneheptanoic acid methyl ester

To a solution of 1.93 g (12 mmol; 1.47 ml) of diethylaminosulfur trifluoride in 30 ml of methylene chloride cooled to −78° C. under a nitrogen atmosphere is added over 30 minutes a solution of 1.49 g (6 mmol) of β-hydroxy-α-methylenebenzeneheptanoic acid methyl ester of Method A, step 1 above, in 30 ml of methylene chloride. After 30 minutes at −78° C., the solution is allowed to rise to room temperature and is maintained with stirring for 1.5 hours.

The solution is diluted with brine and extracted with methylene chloride. The combined organic extracts are washed with brine, dried over magnesium sulfate, filtered and rotoevaporated to give crude product.

Column chromatography on silica gel (hexane:ethyl ether (4:1)) gives 797 ml of the title compound: IR (neat) γ 1721 cm$^{-1}$; NMR (CDCl$_3$) δ 1.28-1.88 (6H, m), 2.52 (2H, t, J=8 Hz), 3.66 (3H, s), 5.2 (1H, ddd, J$_{HF}$=48 Hz and J=3, 9 Hz), 5.83 (1H, s), 6.25 (1H, d, J=3 Hz), 7.09 (3H, m), 7.19 (2H, d, J=8 Hz).

Analysis for: $C_{15}H_{19}FO_2$; Calculated: C, 71.97; H, 7.65; Found: C, 72.07; H, 7.71.

(B) 2(1-Fluoro-5-phenylpentyl)-2-oxiranecarboxylic acid methyl ester (isomer A)

2(1-Fluoro-5-phenylpentyl)-2-oxiranecarboxylic acid methyl ester (isomer B)

A solution of 500 mg (2.0 mmol) of β-fluoro-α-methylbenzene-heptanoic acid methyl ester in 50 ml of 1,2-dichloroethane is treated with 1.38 g (8 mmol) of m- chloroperoxybenzoic acid and 20 mg of 4,4′-thiobis(6-t-butyl-m-cresol). The mixture is heated to reflux and maintained under nitrogen for 10.5 hours. An additional 1.38 g (8 mmol) of m-chloroperoxybenzoic acid and 20 mg of 4,4′-thiobis(6-t-butyl-m-cresol) is added and reflux is continued for 8 hours.

The mixture is diluted with ethyl ether and washed sequentially with aqueous sodium sulfite, aqueous sodium bicarbonate, aqueous sodium sulfite and finally aqueous sodium bicarbonate. The ethereal solution is dried over magnesium sulfate, filtered and evaporated.

The residue is chromatographed preparatively on silica gel (hexane:ethyl ether (3:1)) to give the title compounds of Example 1 (isomer A) (Rf 0.37 in hexane:ethyl ether (3:2)) and isomer B (Rf 0.25 in hexane:ethyl ether (3:2)): IR (neat) γ 1742 cm$^{-1}$; NMR (CDCl$_3$) δ 1.40–1.88 (6H, m), 2.64 (2H, t, J=8 Hz), 2.94 (1H, d, J=6 Hz), 3.13 (1H, dd, J=6 Hz, J$_{HF}$=3 Hz), 3.81 (3H, s), 4.93 (1H, ddd, J$_{HF}$=48 Hz, J=10, 3 Hz), 7.20 (2H, d, J=8 Hz) and 7.31 (2H, d, J=8 Hz).

EXAMPLE 2

2-[5-(4-Chlorophenoxy)-1-fluoropentyl]-2-oxiranecarboxylic acid methyl ester

Method A (A) β-Hydroxy-α-methylene-7-(4-chlorophenoxy)-heptanoic acid methyl ester (1) 5-(4-chlorophenoxy)-1-pentanal To a suspension of 33 g (0.15 mmol) of pyridinium chlorochromate in 450 ml of methylene chloride is added 21.4 g (0.1 mol) of 5-(4-chlorophenoxy)-1-pentanol. The mixture is maintained with stirring for 3 hours, diluted with 900 ml of ethyl ether and stirred for an additional 1 hour.

The mixture is filtered through Florisil to give after rotoevaporation 18.2 g of the title product: IR (neat) 1728, 1493 and 1248 cm$^{-1}$.

(2) β-Hydroxy-α-methylene-7-(4-chlorophenoxy)-heptanoic acid methyl ester

A mixture of 18.0 g (84.6 mmol) of 5-(4-chlorophenoxy)-1-pentanal, 10.9 g (127 mmol) of methyl acrylate and 1.1 g (10 mmol) of 1,4-diazabicyclo[2.2.2]octane is allowed to stand at room temperature for 139 hours.

The excess methyl acrylate is removed from the mixture under a stream of nitrogen and by rotoevaporation. The residual oil is partitioned between ice-cold aqueous 10% hydrochloric acid and ethyl ether. The combined ethereal extracts are washed with ice-cold aqueous 10% hydrochloric acid, dried over magnesium sulfate, filtered and rotoevaporated to give crude product.

Column chromatography on silica gel using hexane:ethyl ether (3:2) as eluent gives 10.3 g of title compound: IR (neat) γ 3460 (broad), 1715, 1491 and 1242 cm$^{-1}$; NMR (CDCl$_3$) δ 1.42–1.94 (6H, m), 2.54 (1H, broad s removed by D$_2$O exchange), 3.78 (3H, s), 3.94 (2H, t, J=7 Hz), 4.45 (1H, t, J=7 Hz), 5.84 (1H, s), 6.27 (1H, s), 6.83 (2H, d, J=8 Hz) and 7.24 (2H, d, J=8 Hz).

(B) 2-[5-(4-Chlorophenoxy)-1-hydroxypentyl]-2-oxiranecarboxylic acid methyl ester (isomer A)

2-[5-(4-Chlorophenoxy)-1-hydroxypentyl]-2-oxiranecarboxylic acid methyl estere (isomer B)

A solution of β-hydroxy-α-methylene-5-(4-chlorophenoxy)heptanoic acid methyl ester (10.3 g; 34.5 mmol) in 100 ml of 1,2-dichloroethane is treated with 100 mg of 4,4′-thiobis(6-t-butyl-m-cresol) and 12.1 g (700 mmol) of m-chloroperoxybenzoic acid. The mixture is heated to reflux under nitrogen for 17 hours.

The mixture is cooled, treated with 10% aqueous sodium sulfite and extracted with ethyl ether. The ethereal extract is washed with aqueous sodium bicarbonate, 10% aqueous sodium sulfite and aqueous sodium bicarbonate. The organic extract is dried over magnesium sulfate, filtered and rotoevaporated to give an oil as a 3:1 mixture (isomer A:isomer B) of the diastereomeric title compounds.

The mixture is separated chromatographically (silica gel; hexane:ethyl ether (3:2)) to give 1.38 g of isomer A (Rf 0.16 in hexane:ethyl ether (1:1)): IR (neat) γ 3520 (broad), 1739, 1493, and 1247 cm$^{-1}$; NMR (CDCl$_3$) δ 1.54–1.71 (2H, m), 1.71 (4H, m), 2.38 (1H, broad s, removed on D$_2$O exchange), 3.03 (1H, d, J=6 Hz), 3.17 (1H, d, J=6 Hz), 3.80 (3H, s), 3.91 (1H, m), 3.97 (2H, t, J=6 Hz), 6.85 (2H, d, J=10 Hz), 7.26 (2H, d, J=10 Hz).

Analysis for: C$_{15}$H$_{19}$ClO$_5$; Calculated: C, 57.23; H, 6.08; Found: C, 56.86; H, 5.99.

and 0.46 g of isomer B (Rf 0.10 in hexane:ethyl ether (1:1)): IR (neat) γ 3480 (broad), 1738, 1497 and 1249 cm$^{-1}$; NMR (CDCl$_3$) δ 1.52–1.96 (6H, m), 2.12 (1H, broad s, removed by D$_2$O exchange), 3.04 (1H, d, J=6 Hz), 3.14 (1H, d, J=6 Hz), 3.80 (3H, s), 3.96 (2H, t, J=6 Hz), 4.18 (1H, m), 6.85 (2H, d, J=9 Hz), 7.16 (2H, d, J=9 Hz).

Analysis for: C$_{13}$H$_{19}$ClO$_5$; Calculated: C, 57.23; H, 6.08; Found: C, 56.69; H, 6.26.

(C) 2-[5-(4-Chlorophenoxy)-1-fluoropentyl]-2-oxiranecarboxylic acid methyl ester (isomer A)

To a solution of 967 mg (6 mmol, 733 μl) of diethylaminosulfur trifluoride in 25 ml of methylene chloride cooled to −78° C. under a nitrogen atmosphere is added dropwise a solution of 945 mg (3 mmol) of 2-[5-(4-chlorophenoxy)-1-hydroxypentyl]-2-oxiranecarboxylic acid methyl ester (isomer A) in 25 ml of methylene chloride over 30 minutes. The mixture is stirred at −78° C. for 30 minutes and then is allowed to come to room temperature. The mixture is stirred at room temperature for 1.5 hours, is quenched with brine and is extracted with ethyl ether. The combined ethereal extracts are dried over magnesium sulfate, filtered and rotoevaporated to give a crude solid. Trituration with cyclohexane:isopropyl ether and subsequent high vacuum drying affords 597 mg of the title compound (isomer A) (Rf 0.45 in hexane:ethyl ether (1:1)): m.p. 76°–78° C.; IR (KBr) γ 1740, 1497, 1257, 832 and 758 cm$^{-1}$; NMR (CDCl$_3$) δ 1.54–2.02 (6H, m), 3.10 (1H, dd, J=3, 6 Hz), 3.18 (1H, d, J=6 Hz), 3.80 (3H, s), 3.96 (2H, t, J=7 Hz), 5.19 (1H, ddd, J$_{HF}$=48 Hz, 10, 3 Hz), 6.85 (2H, d, J=7 Hz) and 7.27 (2H, d, J=7 Hz).

Analysis for: C$_{15}$H$_{18}$FClO$_4$; Calculated: C, 56.88; H, 5.73; Found: C, 55.82; H, 5.65.

2-[5-(4-Chlorophenoxy)-1-fluoropentyl]-2-oxiranecarboxylic acid methyl ester (isomer B)

To a solution of 1.03 g (6.36 mmol, 777 μl) of diethylaminosulfur trifluoride in 25 ml of methylene chloride cooled to −78° C. under a nitrogen atmosphere is added dropwise over 5 minutes a solution of 1.0 g (3.18 mmol) of 2-[5-(4-chlorophenoxy)-1-hydroxypentyl]-2-oxiranecarboxylic acid methyl ester (isomer B) in 10 ml of methylene chloride. The mixture is allowed to warm to room temperature and is stirred for 1.5 hours.

The mixture is cooled in an ice bath and is quenched dropwise with aqueous sodium bicarbonate. The solution is extracted with ethyl ether, and the combined ethereal extracts are dried over magnesium sulfate.

Filtration and rotoevaporation gives 1.0 g of crude product which is subjected to preparative column chromatography on silica gel (hexane:ethyl ester (7:3)). The appropriate fractions (Rf 0.23 (hexane:ethyl ether (3:2)) are combined and rotoevaporated to give 555 mg (55.1%) of the title compound: IR (film 1730 cm$^{-1}$; NMR (CDCl$_3$) δ 1.54–1.96 (6H, mc), 2.97 (1H, d, J=6 Hz), 3.16 (1H, dd, J=6, 2 Hz), 3.83 (3H, s), 3.97 (2H, t, J=8 Hz), 4.98 (1H, ddd, J$_{HF}$=48 Hz, 10, 2 Hz), 6.85 (2H, d, J=10 Hz), 7.28 (2H, d, J=10 Hz).

Analysis for: C$_{15}$H$_{18}$ClFO$_4$; Calculated: C, 56.88; H, 5.73; Found: C, 56.34; H, 5.66.

EXAMPLE 3

2-[6-(4-Chlorophenoxy)-1-fluorohexyl]-2-oxiranecarboxylic acid methyl ester

Method A (A) β-Hydroxy-α-methylene-8-(4-chlorophenoxy)octanoic acid methyl ester (1) 6-(4-chlorophenoxy)-1-hexanal To a suspension of 32 g (0.15 mol) of pyridinium chlorochromate in 450 ml of methylene chloride is added 23 g (0.1 mol) of 6-(4-chlorophenoxy)-1-hexanol. The mixture is maintained under a nitrogen atmosphere for 2 hours, is diluted with 1000 ml of ethyl ether and is stirred for 1.5 hours.

The mixture is filtered through a column of Florisil and neutral alumina using ethyl ether for elution. Rotoevaporation gave 18.9 g of the title compound which is used without characterization.

(2) β-hydroxy-α-methylene-8-(4-chlorophenoxy)octanoic acid

A mixture of 18.9 g (0.083 mol) of 6-(4-chlorophenoxy)-1-hexanal, 21.5 g (0.25 mol) of methyl acrylate and 500 mg of 1,4-diazabicyclo[2.2.2]octane is allowed to stand at room temperature for 112.5 hours (an additional 500 mg of 1,4-diazabicyclo[2.2.2]octane is added after 66 hours and 96 hours). Excess methyl acrylate is removed under a stream of nitrogen to give a crude oil.

Column chromatography on silica gel (hexane:ethyl ether (3:2)) yields 2.7 g of the title compound.

An analytical sample is obtained by preparative layer chromatography (Rf 0.14 in hexane:ethyl ether (3:2)): IR (neat) γ 1713, 1490, 1241 and 819 cm$^{-1}$; NMR (CDCl$_3$) δ 1.30–1.98 (8H, m), 3.80 (3H, s), 3.93 (2H, t, J=8 Hz), 4.42 (1H, t, J=7 Hz), 5.83 (1H, s), 6.26 (1H, s), 6.84 (2H, d, J=9 Hz), and 7.25 (2H, d, J=9 Hz).

Analysis for: C$_{16}$H$_{20}$ClO$_4$; Calculated: C, 61.63; H, 6.47; Found: C, 61.40; H, 6.67.

(B) 2-[6-(4-Chlorophenoxy)-1-hydroxyhexyl]-2-oxiranecarboxylic acid methyl ester (isomer A)

A solution of 1.5 g (5.0 mmol) of β-hydroxy-α-methylene-8-(4-chlorophenoxy)octanoic acid methyl ester in 50 ml of 1,2-dichloroethane is treated with 25 mg of 4,4′-thiobis(6-t-butyl-m-cresol) and 1.73 g (10 mmol) of m-chloroperoxybenzoic acid. The mixture is stirred at room temperature for 2.5 hours. The mixture is heated to reflux under a nitrogen atmosphere and is maintained for 15.5 hours.

The mixture is diluted with methylene chloride and then is washed sequentially with aqueous sodium sulfite and aqueous sodium bicarbonate. The sodium sulfite and sodium bicarbonate washed are repeated and the organic layer is finally dried over magnesium sulfate. Filtration and rotoevaporation gives an oil which is subjected to preparative column chromatography (silica gel; hexane:ethyl ether (1:1)) to give 480 mg of the title compound (isomer A; Rf 0.20 in hexane:ethyl ether (1:1)): NMR (CDCl$_3$) δ 1.22–1.86 (8H, m), 3.01 (1H, d, J=6 Hz), 3.16 (1H, d, J=6 Hz), 3.80 (3H, s), 3.89 (1H, m), 3.92 (2H, d, J=9 Hz) and 7.25 (2H, d, J=9 Hz).

(C) 2-[6-(4-Chlorophenoxy)-1-fluorohexyl]-2-oxiranecarboxylic acid methyl ester (isomer A)

To a solution of 474 mg (2.94 mmol; 359 μl) of diethylaminosulfur trifluoride in 25 ml of methylene chloride cooled to −78° C. under a nitrogen atmosphere is added dropwise over 45 minutes a solution of 480 mg (1.47 mmol) of 2-[6-(4-chlorophenoxy)-1-hydroxyhexyl]-2-oxiranecarboxylic acid methyl ester in 25 ml of methylene chloride. The solution is maintained at −78° C. with stirring for 1.25 hours and then is allowed to warm to room temperature. After 1 hour the solution is quenched with 25 ml of aqueous saturated sodium bicarbonate and is stirred for 30 minutes.

The mixture is then diluted with aqueous sodium bicarbonate and is extracted with ethyl ether. The combined ethereal extracts are dried over magnesium sulfate, filtered and rotoevaporated to give crude product. Column chromatography (silica gel; hexane:ethyl ether (7:3)) affords 432 mg of the title compound (isomer A) (Rf 0.32 in hexane:ethyl ether (3:2)): IR (neat) γ 1735, 1490, and 1242 cm$^{-1}$; NMR (CDCl$_3$) δ 1.42–2.00 (8H, m), 3.09 (1H, dd, J=7, 5 Hz), 3.17 (1H, d, J=7 Hz), 3.80 (3H, s), 3.95 (2H, t, J=6 Hz), 5.18 (1H, ddd, J$_{HF}$=48 Hz) and 6.85 (2H, d, J=9 Hz).

Analysis: C$_{16}$H$_{20}$ClFO$_4$; Calculated: C, 58.09; H, 6.09; Found: C, 57.56; H, 6.08.

2-[6-(4-Chlorophenoxy)-1-fluorohexyl]-2-oxiranecarboxylic acid methyl ester (isomer B)

To a solution of 1.77 g (10.96 mmol, 1.45 ml) of diethylaminosulfur trifluoride in 95 ml of methylene chloride cooled to −78° C. under nitrogen is added dropwise a solution of 1.80 g (5.48 mmol) of 2-[6-(4-chlorophenoxy)-1-hydroxyhexyl]-2-oxiranecarboxylic acid methyl ester (isomer B) over 60 minutes. The mixture is stirred at −78° C. for 75 minutes, is allowed to come to room temperature over 1 hour and is stirred for an additional 1 hour. The mixture is quenched at 0° C. by dropwise addition of aqueous sodium bicarbonate and is stirred for 30 minutes. Dilution with aqueous sodium bicarbonate and extraction with ethyl ether affords, after drying over magnesium sulfate, filtration and rotoevaporation of the combined ethereal extracts, crude product.

Column chromatography on silica gel (hexane:ethyl ether (7:3)) gives 0.25 g (13.8%) of the title compound: IR (film) 1740 cm$^{-1}$; NMR (CDCl$_3$) δ 1.42–1.92 (8H, mc), 2.97 (1H, d, J=6 Hz), 3.16 (1H, dd, J=6, 3 Hz), 3.84 (3H, s), 3.96 (2H, t, J=8 Hz), 4.97 (1H, ddd, J$_{HF}$=48, 10, 2 Hz), 6.86 (2H, d, J=10 Hz), 7.28 (2H, d, J=10 Hz).

Analysis for: C$_{16}$H$_{20}$ClFO$_4$; Calculated: C, 58.09; H, 6.09; Found: C, 57.50; H, 6.10.

EXAMPLE 4

2-[5-(4-Chlorophenoxy)-1-fluoropentyl]-2-oxiranecarboxylic acid sodium salt (isomer A)

A solution of 2-[5-(4-chlorophenoxy)-1-fluoropentyl]-2-oxiranecarboxylic acid methyl ester (2.53 g, 8 mmol) of Example 2 in 25 ml of absolute ethanol is treated with a solution of 320 mg (8 mmol) of sodium hydroxide in 12 ml of water. The mixture is maintained with stirring at room temperature for 2 hours and then is rotoevaporated. The obtained solid is triturated three times with ethyl ether, the solvent is removed by rotoevaporation and the solid is dried at high vacuum over phosphorus pentoxide to give 2.25 g (86.6%) of the title compound: m.p. 159°–175° C.; IR (KBr) 1630, 1608, 1490 and 1242 cm$^{-1}$; NMR (d$_6$-DMSO) δ 1.54 (2H, m), 1.73 (4H, m), 2.65 (1H, m), 2.73 (1H, d, J=6 Hz), 3.98 (2H, t, J=6 Hz), 5.22 (1H, ddd, J$_{HF}$=48, 10, 3 Hz), 7.00 (2H, d, J=9 Hz) and 7.36 (2H, d, J=9 Hz).

Analysis for: C$_{14}$H$_{15}$NaFClO$_4$; Calculated: C, 51.78; H, 4.66; Found: C, 51.37; H, 4.53.

EXAMPLE 5

2-[6-(4-Chlorophenoxy)-1-fluorohexyl]-2-oxiranecarboxylic acid sodium salt (isomer A)

To a suspension of 1.79 g (5.41 mmol) of 2-oxiranecarboxylic acid methyl ester (isomer A) of Example 3 in 5.14 ml of absolute ethanol is added at room temperature 5.14 ml (5.14 mmol) of 1N aqueous sodium hydroxide. After 30 minutes, 4.0 ml of tetrahydrofuran is added to achieve total dissolution and stirring is maintained for 1.25 hours. Evaporation of the solvents and trituration with pentane and isopropyl ether gives 1.46 g (79.7%) of the title compound: m.p. 112°–125° C.; IR (KBr) 1640, 1608 cm$^{-1}$; NMR (d$_6$-DMSO) δ 1.47 (4H, m), 1.74 (4H, m), 2.63 (1H, dd, J=8, 3 Hz), 2.73 (1H, d, J=8 Hz), 3.98 (2H, t, J=9 Hz), 5.19 (1, ddd, J=48, 10, 2 Hz), 6.98 (2H, d, J=8 Hz) and 7.32 (2H, d, J=8 Hz).

Analysis for: C$_{15}$H$_{17}$ClFO$_4$Na; Calculated: C, 53.19; H, 5.06; Found: C, 51.22; H, 5.03.

EXAMPLE 6

2-[5-(4-Chlorophenoxy)-1,1-difluoropentyl]-2-oxiranecarboxylic acid methyl ester 2-[5-(4-Chlorophenoxy)-1-fluoro-1-pentenyl]-2-oxiranecarboxylic acid methyl ester (A)   2-[5-(4-Chlorophenoxy)-1-oxopentyl]-2-oxiranecarboxylic acid methyl ester To a suspension of 9.05 g (42 mmol) of pyridinium chlorochromate and 3.4 g (42 mmol) of sodium acetate in 150 ml of methylene chloride is added 2.2 g (7 mmol) of 2-[5-(4-chlorophenoxy)-1-hydroxypentyl]-2-oxiranecarboxylic acid methyl ester of Example 2, part 2. The mixture is stirred for 4 hours, is diluted with ethyl ether and filtered through Florisil. The solution is rotoevaporated and is chromatographed preparatively on silica gel using hexane:ethyl ether (3:2) as eluting solvent. The appropriate fractions are combined, washed with aqueous copper sulfate and brine and dried over magnesium sulfate. Filtration and rotoevaporation gives crude product. Column chromatography (silica gel; hexane:ethyl ether (3:2)) affords 523 mg (23.9%) of the title compound: IR (film) 1746, 1717 cm$^{-1}$; NMR (CDCl$_3$) δ 1.80 (4H, m), 2.66 (2H, m), 3.08 (1H, d, J=6 Hz), 3.34 (1H, d, J=6 Hz), 3.84 (3H, s), 3.94 (2H, t, J=6 Hz), 6.82 (2H, d, J=10 Hz) and 7.24 (2H, d, J=10 Hz).

Analysis for: C$_{15}$H$_{17}$ClO$_5$; Calculated: C, 57.60; H, 5.48; Found: C, 57.41; H, 5.56.

(B)   2-[5-(4-Chlorophenoxy)-1,1-difluoropentyl]-2-oxiranecarboxylic acid methyl ester 2-[5-(4-Chlorophenoxy)-1-fluoro-1-pentenyl]-2-oxiranecarboxylic acid methyl ester To a solution of 6.48 g (40 mmol, 5.31 ml) of diethylaminosulfur trifluoride in 50 ml of anhydrous glyme is added at room temperature 3.13 g (10 mmol) of 2-[5-(4-chlorophenoxy)-1-oxopentyl]-2-oxiranecarboxylic acid methyl ester. The mixture is heated in an oil bath maintained at 110° C. for 4 hours.

The mixture is cooled to ice-bath temperature and is quenched with aqueous ice-cold sodium bicarbonate. The mixture is extracted with ethyl ether and the combined ethereal extracts are dried over magnesium sulfate, filtered and rotoevaporated to give crude products.

The crude material is subjected to preparative HPLC (gradient elution from hexane through hexane:ethyl acetate (95:5)) twice to give 551 mg (16.5%) of 2-[5-(4-chlorophenoxy)-1,1-difluoropentyl]-2-oxiranecarboxylic acid methyl ester (Rf 0.47 hexane:ethyl ether (1:1)): m.p. 40°–48° C., IR (KBr) 1741 cm$^{-1}$; NMR (CDCl$_3$) δ 1.75 (2H, m), 1.85 (2H, m), 2.29 (2H, m), 3.16 (1H, dd, J=6, 2 Hz), 3.23 (1H, d, J=6 Hz), 3.84 (3H, s), 3.97 (2H, t, J=7 Hz), 6.85 (2H, d, J=9 Hz), 7.28 (2H, d, J=9 Hz).

Analysis for: C$_{15}$H$_{17}$ClF$_2$O$_4$; Calculated: C, 53.82; H, 5.12; Found: C, 53.66; H, 5.06.

and 487 mg (15.5%) of oil 2-[5-(4-chlorophenoxy)-1-fluoro-1-pentenyl]-2-oxiranecarboxylic acid methyl ester (Rf 0.42 in hexane:ethyl ether (1:1)): IR (film) 1748, 1488 and 1240 cm$^{-1}$; NMR (CDCl$_3$) δ 1.89 (2H, p, J=9 Hz), 2.37 (2H, m), 3.12 (1H, d, J=7 Hz), 3.29 (1H, dd, J=7, 2 Hz), 3.82 (3H, s), 3.96 (2H, t, J=6 Hz), 5.24 (1H, dt, J=36, 8 Hz), 6.85 (2H, d, J=8 Hz) and 7.27 (2H, d, J=8 Hz).

Analysis for: C$_{15}$H$_{16}$ClFO$_4$; Calculated: C, 57.24; H, 5.12; Found: C, 58.99; H, 5.80.

EXAMPLE 7

2-[6-(4-Chlorophenoxy)-1,1-difluorohexyl]-2-oxiranecarboxylic acid methyl ester

2-[6-(4-Chlorophenoxy)-1-fluoro-1-hexenyl]-2-oxiranecarboxylic acid methyl ester (A)   2-[6-(4-Chlorophenoxy)-1-oxohexyl]-2-oxiranecarboxylic acid methyl ester To a suspension of 11.6 g (54 mmol) of pyridinium chlorochromate and 4.4 g (54 mmol) of sodium acetate in 200 ml of methylene chloride is added 2.95 g (9 mmol) of 2-[6-(4-chlorophenoxy)-1-hydroxyhexyl]-2-oxiranecarboxylic acid methyl ester (isomer A) prepared according to the procedure of Example 2, part 2, at room temperature under a nitrogen atmosphere. The mixture is stirred for 4 hours, is diluted with 600 ml of ethyl ether and is filtered through Florisil. Rotoevaporation gives 2.2 g of crude product. Preparative column chromatography (silica gel:ethyl ether (3:2)) affords 1.66 g (56.4%) of the title compound: IR (film) 1746, 1719 cm$^{-1}$; NMR (CDCl$_3$) δ 1.49 (2H, p, J=8 Hz), 1.62–1.86 (4H, mc), 2.62 (2H, m), 3.05 (1H, d, J=6 Hz), 3.36 (1H, d, J=6 Hz), 3.86 (3H, s) 3.94 (2H, t, J=6 Hz), 6.84 (2H, d, J=8 Hz) and 7.27 (2H, d, J=8 Hz).

Analysis for: C$_{16}$H$_{19}$ClO$_5$; Calculated: C, 58.81; H, 5.86; Found: C, 58.99; H, 5.80.

(B)   2-[6-(4-Chlorophenoxy)-1,1-difluorohexyl]-2-oxiranecarboxylic acid methyl ester 2-[6-(4-Chlorophenoxy)-1-fluoro-1-hexenyl]-2-oxiranecarboxylic acid methyl ester To a solution of 1.29 g (8 mmol, 1.06 ml) of diethylaminosulfur trifluoride in 50 ml of anhydrous glyme is added 1.31 g (4 mmol) of 2-[6-(4-chlorophenoxy)-1-oxohexyl]-2-oxiranecarboxylic acid methyl ester. The mixture is heated to reflux under nitrogen for 2.5 hours. An additional 2.58 g (16 mmol, 2.1 ml) of diethylaminosulfur trifluoride is added and reflux is continued for 5.5 hours. The mixture is allowed to come to room temperature for 16 hours and is then heated to reflux for 3 hours. The mixture is cooled to ice-bath temperature and is quenched dropwise with saturated aqueous sodium bicarbonate. The mixture is extracted with ethyl ether and the combined ethereal extracts are dried over magnesium sulfate. Filtration and rotoevaporation gives an oil which crystallizes upon overnight refrigeration. The solid is triturated and crystallized from hexane:cyclohexane (1:1) to give a crude solid (m.p. 44°–46° C.).

Flash chromatography on silica (230–400 mesh) utilizing hexane:benzene:ethyl acetate (12:5:2) as eluting solvent gives 250 mg (23.3%) of 2-[6-(4-chlorophenoxy)-1,1-difluorohexyl]-2-oxiranecarboxylic acid methyl ester (Rf 0.54 in hexane:ethyl ether (1:1)): m.p. 54°–55° C.; IR (KBr) 1740 cm$^{-1}$; NMR (CDCl$_3$) δ 1.79 (6H, mc), 1.83 (2H, p, J=8 Hz), 2.26 (2H, m), 3.16 (1H, dd, J=6, 2 Hz), 3.24 (1H, J=6 Hz), 3.85 (3H, s), 3.96 (2H, t, J=8 Hz), 6.86 (2H, d, J=10 Hz) and 7.48 (2H, d, J=10 Hz).

Analysis for: $C_{16}H_{19}ClF_2O_4$; Calculated: C, 55.10; H, 5.49; Found: C, 55.03; H, 5.47.

and a crude oil which is subjected sequentially to preparative flash chromatography (silica gel; hexane:benzene:ethyl acetate (13:6:1)) and preparative layer chromatography (silica gel; toluene:hexane (9:1)). Obtained is 63 mg (4.8%) of 2-[6-(4-chlorophenoxy)-1-fluoro-1-hexenyl]-2-oxiranecarboxylic acid methyl ester (Rf 0.46 in hexane:ethyl ether (1:1)): IR (film) 1740 cm$^{-1}$; NMR (CDCl$_3$) δ 1.60 (2H, m), 1.82 (2H, m), 2.27 (2H, m), 3.14 (1H, d, J=6 Hz), 3.29 (1H, dd, J=6, 2 Hz), 3.86 (3H, s), 3.96 (2H, t, J=7 Hz), 5.22 (1H, dt, J$_{HF}$=36, J=7 Hz), 6.85 (2H, d, J=9 Hz), 7.28 (2H, d, J=9 Hz)

Analysis for: $C_{16}H_{18}ClFO_4$; Calculated: C, 58.45; H, 5.52; Found: C, 58.52; H, 5.56.

EXAMPLE 8

2-[6-(4-Chlorophenoxy)-1,1-difluorohexyl]-2-oxiranecarboxylic acid sodium salt

A solution of 348 mg (1 mmol) of 2-[6-(4-chlorophenoxy)-1,1-difluorohexyl]-2-oxiranecarboxylic acid methyl ester of Example 7 in 10 ml of 95% ethanol is treated with a solution of 40 mg (1 mmol) of sodium hydroxide in 5 ml of water. The solution is stirred at room temperature for 3 hours and is then rotoevaporated. The obtained solid is triturated two times with ethyl ether and the solvent is removed to give 289 mg (77.1%) of the title compound: m.p. 140°–153° C.; IR (KBr) 1645, 1618 cm$^{-1}$; NMR (d$_6$-DMSO) δ 1.46 (4H, m), 1.73 (2H, p, J=7 Hz), 2.42 (2H, m), 2.70 (1H, d, J=7 Hz), 2.76 (1H, d, J=7 Hz), 3.98 (2H, t, J=7 Hz), 7.00 (2H, d, J=10 Hz) and 7.36 (2H, d, J=10 Hz).

Analysis for: $C_{15}H_{16}ClF_2NaO_4$; Calculated: C, 48.07; H, 4.84; Found: C, 48.13; H, 4.47.

EXAMPLE 9

2-(5-Phenyl-1-oxopentyl)-2-oxiranecarboxylic acid methyl ester

To a suspension of 7.6 g (35.4 mmol) of pyridinium chlorochromate and 2.90 g (35.4 mmol) of anhydrous sodium acetate in 100 ml of methylene chloride is added 1.55 g (5.9 mmol) of 2-(5-phenyl-1-hydroxypentyl)-2-oxiranecarboxylic acid methyl ester. The mixture is stirred at room temperature for 3 hours and then is diluted with ethyl ether. Filtration through Florisil and rotoevaporation gives an oil which is subjected to preparative column chromatography on silica gel (hexane:ethyl ether (3:2)). The appropriate fractions are combined and rotoevaporated to give 670 mg (43.3%) of the title compound: IR (film) 1757, 1723 cm$^{-1}$; NMR (CDCl3) δ 1.65 (4H, m), 2.48–2.65 (4H, mc), 3.06 (1H, d, J=6 Hz), 3.33 (1H, d, J=6 Hz), 3.83 (3H, s), 7.21 (3H, m), 7.30 (2H, m).

Analysis for: $C_{15}H_{18}O_4$; Calculated: C, 68.68; H, 6.92; Found: C, 68.55; H, 7.13.

EXAMPLE 10*

2-[5-(4-Chlorophenyl)pentyl]-2-oxiranecarboxylic acid ethyl ester (A) 2-[5-(4-Chlorophenyl)pentyl]-2-oxiranecarboxylic acid ethyl ester 8.8 g of the title compound (b.p. 135° to 140° C. under 0.005 mm Hg) are obtained from 15 g of 7-(4-chlorophenyl-2-methylene heptanoic acid ethyl ester and 23 g of m-chloroperbenzoic acid in 180 ml of methylene chloride.

(B) 7-(4-Chlorophenyl)-2-methyleneheptanoic acid ethyl ester 15.5 g of 7-(4-chlorophenyl)-2-methyleneheptanoic acid ethyl ester (b.p. 140° to 145° C. under 0.008 mm Hg) are obtained from 25 g of 5-(4-chlorophenyl)pentylmalonic acid ethyl ester, 3.8 g of paraformaldehyde, 16 ml of pyridine and 1 ml of piperidine.

(C) 5-(4-Chlorophenyl)pentylmalonic acid ethyl ester 26.5 g of 5-(4-chlorophenyl)pentylmalonic acid ethyl ester are obtained as a viscous oil from 34 g of 5-(4-chlorophenyl)pentylmalonic acid diethyl ester and 5.7 g of potassium hydroxide in 150 ml of ethanol.

(D) 5-(4-Chlorophenyl)pentylmalonic acid diethyl ester 35.5 g of 5-(4-chlorophenyl)pentylmalonic acid diethyl ester are obtained as an oil from 70.5 g of p-toluenesulfonic acid [5-(4-chlorophenyl)-pentyl] ester 32 g of malonic acid diethyl ester and a solution of 4.6 g of sodium in 250 ml of ethanol.

* This preparative description is Example 11 of U.S. Pat. No. 4,324,796.

EXAMPLE 11*

2-[6-(4-Chlorophenoxy)hexyl]-2-oxiranecarboxylic acid ethyl ester (A) 2-[6-(4-Chlorophenoxy)hexyl]oxirane-2-carboxylic acid ethyl ester 5.5 g of the title compound [colorless oil of b.p. 164° C. at 0.2 mm Hg (26.6 Pa)] are obtained from 15.0 g of 8-(4-chlorophenoxy)-2-methyleneoctanoic acid ethyl and 14.72 g m-chloroperbenzoic acid in 50 ml of methylene chloride.

(B) 8-(4-Chlorophenoxy)-2-methyleneoctanoic acid ethyl ester 52.1 g of 8-(4-chlorophenoxy)-2-methyleneoctanoic acid ethyl ester [b.p. 171° C. at 0.1 mm Hg (13.3 Pa)] are obtained from 74 g of 6-(4-chlorophenoxy)hexylmalonic acid ethyl ester, 8.2 g of paraformaldehyde, 41 ml of pyridine and 2.8 ml of piperidine.

(C) 6-(4-Chlorophenoxy)hexylmalonic acid ethyl ester (Yellowish viscous oil) are obtained from 83.5 g of 6-(4-chlorophenoxy)hexylmalonic acid diethyl ester and 14.4 of potassium hydroxide in 500 ml of ethanol.

(D) 6-(4-Chlorophenoxy)hexylmalonic acid diethyl ester 87 g of 6-(4-chlorophenoxy)hexylmalonic acid diethyl ester ([b.p. 173° C. at 0.1 mm Hg (13.3 Pa)] are obtained from 106.7 g of 6-(4-chlorophenoxy)hexylbromide, 53.8 g of malonic acid diethyl ester and a solution of 8.4 g of sodium in 350 ml of ethanol.

*This preparative description is Example 7 of U.S. Pat. No. 4,337,267.

EXAMPLE 12

This ability of the compounds in the scope of the invention to inhibit the activity of cell free platelet PLA$_2$ enzyme is measured in the following in vitro assay.

The assay is carried out as follows:

Substrate Preparation

E. coli, cultured to exponential growth, are sedimented for 15 minutes at 10,000 g and resuspended in sterile isotonic saline (1–3 ml). 10–25 μCi uniformly labeled [$^3$H]-arachidonic acid (AA) is added to a sterile flask, evaporated by N$_2$ and resolubilized with 0.3 ml 20% fatty acid-free bovine serum albumen (BSA). 75–100 ml of nutrient broth and 1 ml E. coli are then added to each flask and incubated for 2–3 hours at 37° C. [$^3$H]-AA labelled E. coli are then sedimented, suspended in saline and added to fresh nutrient broth and incubated for 1.5 hours at 37° C. to complete [$^3$H]-AA incorporation into the phospholipids. After overnight refrigeration of cultures, E. coli are again sedimented, suspended in saline and autoclaved for 15 minutes at 120° C. E. coli cultures are washed twice with saline (first wash contains 1% BSA) and resupended in saline. Non-labelled E. coli cultures are also prepared in the same manner. Cell number is determined by measuring the optical density at 550 nm ($3\times10$ cell/ml=1 O.D.). The amount of radioactivity associated with cells is determined by counting a defined volume of cell suspension. The specific activity is subsequently adjusted by adding non-labelled E. coli to yield $2-4\times10$ cpm per $1\times10^{10}$ E. coli.

Platelet PLA$_2$ Preparation

Expired human platelets from the blood bank are centrifuged for 15 minutes at 200 g to obtain a platelet rich fraction and to remove the red blood cells. Platelets are sedimented for 15 minutes at 2500 g and the plasma is removed before adding cold 0.18N H$_2$SO$_4$ (4 ml/unit). Platelets are homogenized, incubated for 1 hour at 4° C., homogenized again and centrifuged for 15 minutes at 10,000 g. The PLA$_2$ enriched supernatant fluid is removed and the amount of protein is determined by the Lowry method. The preparation is divided into various portions and stored at −20° C.

Assay of PLA$_2$ Activity

The assay measures the hydrolysis of E. coli membrane phospholipids and the release of free [$^3$H]-AA from the C-2 position of phospholipids by human platelet PLA$_2$. To ice cold $15\times100$ mm test tubes, the following additions are made; $2.5\times10^8$ E. coli (equivalent to 5 nmol phospholipid), 5 mM Ca++, 100 mM Tris buffer (pH=7.4), 100 μg platelet extract (or an amount to produce 20–30% hydrolysis), drug or vehicle. Incubations are carried out at 37° C. in a shaking water bath for 30 minutes. The reaction is terminated by the addition of 2 volumes of tetrahydrofuran (THF) and the mixture is vortexed. Hydrolyzed [$^3$H]-AA is separated from unhydrolyzed phospholipid by solid phase extraction using Bond elute NH$_2$ columns (Analytichem Internat.). Columns are conditioned with 0.5 ml THF followed by 0.5 ml THF:H$_2$O (2.0:0.1 ml v/v). Samples are loaded onto columns and hydrolyzed [$^3$H]-AA is eluted with 1 ml THF:glacial acetic acid (98.0:2.0 ml v/v). The elutant is transferred to vials, 10 ml Optifluor is added and the radioactivity is determined by liquid scintillation counting.

Treatments are corrected for non-enzymatic hydrolysis by substracting the dpms in treatments containing no enzyme. Mean [$^3$H]-AA dpm is determined and a percent inhibition relative to vehicle treated samples is calculated.

The percent hydrolysis is calculated by the following equation:

$$\% \text{ Hydrolysis} = \frac{\text{free fatty acid (dpm)}}{\text{total phospholipid + free fatty acid (dpm)}}$$

$$\frac{\text{Rate of}}{\text{Hydrolysis}} = \frac{\% \text{ hydrolysis} \times \text{total phospholipid content (5 nmol)}}{\text{incubation time (min)}}$$

Activity of standard drugs:

| Drug | Inhibition of PLA$_2$ Activity IC$_{50}$, μM |
|---|---|
| para-Bromophenacyl bromide | 23.7 |
| Arachidonic Acid | 10.1 |

When tested in the above-described assay, the compounds of the invention gave the following results:

TABLE 1

| Compound of Example No. | % Inhibition of PLA$_2$(at 50 μM) | IC$_{50}$, μM |
|---|---|---|
| 1 (isomer A) | 88 | 2.6 |
| 2 (isomer A) | 83.8 | 13.8 |
| 3 (isomer A) | 84.6 | 19.2 |
| 6 (gem-difluoro compound) | 91.1 | 8.4 |
| 6 (fluoro-vinyl compound) | 99.5 | 3.0 |
| 6A | 83.2 | 10.7 |
| 7 (gem-difluoro compound) | 82.0 | 11.3 |
| 7A | 88.4 | 7.1 |
| 9 | 81.8 | 3.2 |
| 10 | 97.2 | 1.6 |

The results show the compounds of the invention to have significant PLA$_2$ inhibitory activity in the assay in question.

EXAMPLE 13

The compounds 5- and 12-hydroxyeicosatetraenoic acid (5-HETE and 12-HETE) and LTB$_4$ are early arachidonic acid oxidation products in the lipoxygenase cascade, which have been shown to mediate several aspects of inflammatory and allergic response. This is especially true with respect to 5,12-diHETE, which is also denoted as LTB$_4$ [see Ford-Hitchinson, J. Roy. Soc. Med., 74, 831 (1981)]. Compounds which inhibit the PLA$_2$-mediated release of arachidonic acid thereby effectively prevent the oxidation of arachidonic acid to the various leukotriene products via the lipoxygenase cascade. Accordingly, the specificity of action of PLA$_2$ inhibitors can be determined by the activity of test compounds in this assay, which measures the ability of compounds to inhibit the synthesis of LTB$_4$ by rat glycogen-elicited polymorphonuclear leukocytes (PMN).

The assay is carried out as follows:

Rat polymorphonuclear leukocytes (PMNs) are obtained from female Wistar rats (150–200 g) which receive an injection of 6% glycogen (10 ml i.p.). Rats are sacrificed 18–24 hours post injection by CO$_2$ asphyxiation and the elicited cells are harvested by peritoneal lavage using physiological saline (0.9% NaCl). The exudate is centrifuged at $400\times$g for 10 minutes. The supernatant fluid is discarded and the cell pellet is resuspended to concentration of $2.0 \times 10^7$ cells/ml in HBSS containing $Ca^{++}$ and $Mg^{++}$ and 10 μM L-cysteine.

To 1 ml aliquots of cell suspension, test drugs or vehicle are added, then preincubated at 37° C. for 10 minutes. A23187 (1 μM) and [$^3$H]-AA (3.0 μCi/ml) are then added and the samples are further incubated for 10 minutes. The reaction is terminated by centrifugation and pelleting cells. Supernatants are then analyzed by HPLC analysis on a 15 cm ×4.6 mm ID Supelcosil LC-18 (Supelco)(3M) column, using a two solvent system at a flow rate of 1.4 ml total flow as follows:
Solvent A: 70:30 17.4 mM $H_3PO_4$:$CH_3CN$
Solvent B: $CH_3CN$
Gradient: (system is equillibrated with Solvent A)

| Time | Percent A | Percent B |
| --- | --- | --- |
| 0 | 100 | 0 |
| 15.0 | 100 | 0 |
| 20.0 | 65 | 35 |
| 40.0 | 65 | 35 |
| 42.0 | 10 | 90 |
| 50.0 | 10 | 90 |
| 50.1 | 100 | 0 |

Percent solvent changes are accomplished in a linear fashion.

Injections: 150 μl of each supernatant is injected directly onto column and $^3$H arachidonic acid metabolites are monitored using an on-line radioactivity detector (Ramona, IN/US, Fairfield, N.J.).

Standards: $10^4$–$2.0 \times 10^4$ dpm of eicosanoids of interest are injected in 90 μl EtOH cocktail.

Co-chromatography with standard [$^3$H] leukotriene $B_4$ ($LTB_4$) in medium of stimulated PMN exposed to drug is compared to that found in medium of stimulated cells exposed to no drug, generating percent inhibition.

Results are expressed as percent inhibition at a given compound dose.

Testing compounds in the scope of the invention in this assay give the following results:

TABLE 2

| Compound of Example Number | % Inhibition (at 10 μM) |
| --- | --- |
| 3 | 17 |
| 6 (gem-difluoro compound) | 7 |
| 6 (fluoro-vinyl compound) | 15 |
| 6A | 11 |
| 7 (gem-difluoro compound) | 58 |
| 7A | 30 |
| 9 | 7 |
| 10 | 23 |

The results show that compounds in the scope of this invention have very low activity in this assay.

EXAMPLE 14

The procedure of Example 13 is also employed for the determination of the extent to which compounds in the scope of the invention inhibit the synthesis of the arachidonic acid cyclooxygenase oxidation product $TxB_2$.

In this assay, the procedure of Example 13 is carried out as described. However, in order to determine cyclooxygenase activity, the samples are co-chromatographed with authentic reference [$^3$H]—$TxB_2$.

The results are calculated as in Example 13 and present below:

TABLE 3

| Compound of Example Number | % Inhibition (at 10 μM) |
| --- | --- |
| 3 | 34 |
| 6 (gem-difluoro compound) | 44 |
| 6 (fluoro-vinyl compound) | 33 |
| 6A | 30 |
| 7 (gem-difluoro compound) | 43 |
| 7A | 38 |
| 9 | +1 |
| 10 | +4 |

The results show that the compounds tested show low activity in inhibiting the synthesis of the arachidonic acid cyclooxygenase oxidation product $TxB_2$.

EXAMPLE 15

The ability of the compounds in the scope of the invention to inhibit inflammatory responses is examined in the in vivo arachidonic acid (AA)-/12-O-tetradecanoylphorbol acetate (TPA)-induced murine ear edema According to this test, Swiss Webster female mice (Buckshire), approximately 8 weeks old, are placed into plastic boxes in groups of six. Eight groups of mice receive AA topically on the right ear, and another 8 groups receive TPA topically on the right ear. AA and TPA are dissolved in acetone at concentrations of 100 mg/ml and 100 μg/ml respectively. The pholgistics are applied to the right ear by the means of an automatic pipet. Volumes of 10 μl are applied to the inner and outer surfaces of the ear. Each mouse receives either 2 mg/ear AA or 4 μg/ear TPA. The left ear (control) receives acetone delivered in the same manner. Topical dosing regimes are as follows: (1) drugs are given 30 minutes prior to AA treatment, and (2) drugs are given 30 minutes after treatment with TPA.

Measurements are taken with Oditest calipers, 0–10 mm with 0.01 graduations. The right and left ears are measured 1 hour after AA-induced inflammation and 4 hours after TPA-induced inflammation.

The difference between right and left ear thickness is calculated and the significance is determined by a one way analysis of variance with Dunnett's comparisons to control (P=0.05). Drug effects are expressed as a percent change from control values:

% change from control =

$$\frac{(Rt.\ ear\ -\ Lt.\ ear)drug\ -\ (Rt.\ ear\ -\ Lt.\ ear)control}{(Rt.\ ear\ -\ Lt.\ ear)control}$$

The results for the compounds of the invention are presented in Table 4.

TABLE 4

| | Mouse Ear Edema Assay % Change from Control TOPICAL[a] | |
| --- | --- | --- |
| Compound of Example No. | AA | TPA |
| 6A | −38 | −42 |
| 7A | −59 | −70 |
| 10 | −73 | −45 |

[a] 1 mg/ear

The results show that the compounds in the scope of the invention tested demonstrate topical activity against AA- and TPA-induced mouse ear edema, evidencing an inhibitory effect on acute skin inflammation mediated by products of the lipoxygenase and/or cyclooxygenase pathway.

EXAMPLE 16

The compounds in the scope of the invention are further tested in the rat carrageenan paw edema to determine their ability to inhibit the acute inflammatory response.

This assay is carried out as follows:

140–180 mg male Sprague-Dawley rats, in groups of 6 animals are injected subcutaneously in the right paw with 0.1 ml of 1% carrageenan at zero time. Mercury plethysmographic readings (ml) of the paw made at zero time and 3 hours later. Test compounds are suspended or dissolved in 0.5% methylcellulose and given perorally 1 hour prior to carrageenan administration.

The increase in paw volume (edema in ml.) produced by the carrageenan is measured. Paw edema is calculated (3 hour volume minus zero time volume), and percent inhibition of edema is determined. Unpaired Student's t-test is used to determine statistical significance.

The activity of standard drugs in this assay is as follows:

| Drug | Oral ED$_{50}$ (95% C.L.) mg/kg |
|---|---|
| Indomethacin | 3.7 (0.6, 23.8) |
| Aspirin | 145.4 (33.1, 645.6) |
| Phenylbutazone | 26.2 (2.3, 291.0) |

When tested in this assay, the compounds in the scope of the invention gave the following results:

TABLE 5

| Compound of Example No. | % Inhibition at 50 mg/kg (peroral) |
|---|---|
| 6 (fluoro-vinyl compound) | 26 |
| 6A | 50 |
| 7A | 53 |
| 9 | 27 |
| 10 | 42 |

The results show that the compounds tested have oral activity in the rat carrageenan paw edema assay, evidencing an effect on the acute inflammatory response.

EXAMPLE 17

The assay of this Example is used to determine the oral activity of PLA$_2$ inhibitors by reduction of vascular cutaneous permeability induced by snake venom PLA$_2$.

The assay is carried out as follows:

On day 1, the dorsal area of male Hartley guinea pigs weighing 300–500 g is shaved and the animals are fasted. The next day, the animals are dosed intravenously into the cephalic vein with 120 mg/kg (compound solubilized in DMSO and then mixed with saline to give a 50% DMSO solution) of test compound with vehicle and immediately injected intracardially with a solution of $^{125}$I-BSA at 6 $\mu$Ci/kg/ml of Evans blue; Evans blue at 35 mg/ml of buffered saline). The animals are orally dosed with drug or vehicle 1–2 hours prior to the intracardial injection of $^{125}$I-BSA/EB solution. The animals are then anesthetized with a 25 mg/kg intramuscular injection of ketamine five minutes prior to PLA$_2$ injection. The animals are injected intradermally with buffered saline (pH 7.4) (vehicle control) or Naja mocambique mocambique PLA$_2$ at levels of 50, 10 and 3 $\mu$g/50 $\mu$l/site at two sites per guinea pig. To allow for maximal response, the animals are sacrificed by CO$_2$ asphyxiation thirty minutes after the intradermal injections.

The dorsal skin is reflected back and the area of each injection is excised. One piece of skin is also taken from unaffected areas. The skin plugs are placed in 12×75 mm tubes and the $^{125}$I-BSA in tissue is quantitated by gamma counting. The plugs are then removed from the tubes, placed on a grid tray, covered with a screen and dried in a vacuum oven at 80° C. for one hour. The dry skin weights are recorded.

The counts per minute per skin dry weights and per $^{125}$I-BSA in 500 $\mu$l of blood are normalized and the results expressed as counts per minute/0.1 gm of tissue. The percent of inhibition is calculated from comparisons between counts in the drug-treated group relative to control The activity of standard drugs in this assay is as follows:

| Drug | Dose (mg/kg) p.o. | % Inhibition |
|---|---|---|
| BW 755c | 200 | 65.3 |
| Indomethacin | 50 | 15.0 |
| Chlorpheniramine | 2 | 45.0 |
| Dexamethasone | 10 | 49.0 |

When tested in this assay, compounds in the scope of the invention give the following result:

TABLE 6

| Compound of Example | % Inhibition, iv at 100 mg/kg |
|---|---|
| 6 (fluoro-vinyl compound) | 32 |
| 10 | 24.1 |

The results show that compounds in the scope of the invention exhibit inhibitory activity against inflammation directly initiated by PLA$_2$.

EXAMPLE 18

The assay of this Example measures the ability of the compound in the scope of the invention to inhibit oxazolone-induced contact hypersensitiveity in the mouse ear.

The assay is carried out as follows:

Female, Swiss Webster mice (8 weeks old) are placed into groups of 6 and the abdominal area of each is shaved. The mice are sensitized to oxazolone (4-ethoxymethylene-2-phenyl-oxazol-5-one) by applying 100 $\mu$l of a 2% solution in 95% alcohol directly onto the shaved abdomen using an automatic pipette and rubbing the residual oxaxolone into the skin with a round wooden stick. Six days after sensitization each mouse is challenged by applying 20 $\mu$l if a 2% oxazolone solution in 95% alcohol to the right ear (10 $\mu$l of alcohol alone to the left ear. Compounds for topical applications are prepared in acetone and administered to the right ear 30 min after challenge or 30 min prior to and 5 h after challenge; acetone (vehicle) is applied to the left ear. Compounds for oral administration are suspended in 0.5 ml of 0.5% methyl cellulose and given ten min prior to challenge. Ear thickness of both ears is measured in mm×10$^{-2}$ at 24 and 48 h after challenge using an Oditest caliper. Edema is calculated by subtracting the left ear thickness from the right ear thickness. Drug effects are determined by calculating the percentage change from control for each time period.

When tested in this assay, compounds in the scope of the invention give the following results:

TABLE 7

| Compound of Example No. | % Inhibition* |
|---|---|
| 6A | 34.3 |
| 9 | 22.0 |

*Compound dosed at 1 mg/ear

The results show that the compounds tested exhibit significant inhibitory activity in this assay.

EXAMPLE 19

The assay of this Example measures the in vivo ability of the compounds in the scope of the invention to inhibit the bronchospasm induced in guinea pigs by endogenous mediators of the bronchosonstriction.

The assay is carried out as follows:

Male Hartley strain guinea pigs weighing 250–350 g are utilized to chicken obalbumin (OA) (10 mg i.p.) on days 1 and 3 and used starting on day 26. The animals are anesthetized with pentobarbital sodium (50 mg/kg, i.p.), bilateral vagotomy is performed, and the jugular vein is cannulated for injection of drugs and the carotid artery for monitoring blood pressure. The trachea is cannulated for artificial ventilation by miniature Starling pump and for indirect measurement of respiratory volume changes as described, infra. Succinylcholine (2 mg/kg, i.v.) is administered to arrest spotaneous respiration. A cyclooxygenase inhibitor, indomethacin (10 mg/kg in tris buffer, i.v. at 9 min.) is administered to shunt arachidonic metabolism to lipoxygenase pathways. One minute later, chlorpheniramine (1.0 mg/kg in saline, i.v.) is given to attenuate the histaminic component of anaphylactic bronchoconstriction. Test drugs (dissolved in propylene glycol, polyethylene glycol or saline) are administered either intraduodenally, 10 minutes before antigen challenge. Anaphylactic bronchoconstriction is induced by administration by breaths of aerosolized OA (1%) or by intravenous administration of 1–0.3 mg/kg OA in saline. Control animals receive solvent (2 ml/kg i.d. or appropriate aerosol) in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at minutes 1, 3 and 5 are obtained from the recorded charts.

Area under the volume overflow curve (AUC) is estimated, using the overflow values at 1, 3 and 5 minutes, and expressed as a percentage of the maximal overflow AUC (equation 1):

$$\% \text{ max AUC} = \frac{3(1 \text{ min}) + 4(3 \text{ min}) + 2(5 \text{ min})}{10(\text{max})} \times 100 \quad (1)$$

Drug effects are reported as percent inhibition of % max AUC values obtained from appropriate control animals (equation 2):

$$\% \text{ inhibition} = \quad (2)$$

$$\frac{\% \text{ max AUC control} - \% \text{ max AUC treated}}{\% \text{ max AUC control}} \times 100$$

Students t-test for unpaired data is used to determine statistical significance. Dose response curves are generated and ED$_{50}$ doses are interpolated from the regression lines.

The results for a compound in the scope of the invention in this assay, using ovalbumin for induction of bronchospasm, are given below:

TABLE 8

| Compound administered at 10 minutes before intravenously administered ovalbumin challenge | |
|---|---|
| Compound of Example Number | ED$_{50}$ |
| 6A | 13.5* |

* = intraduodenally administered

The results show that the compound tested has in vivo activity in inhibiting ovalbumin induced bronchospasm mediated by endogenous products of the lipoxygenase oxidation of arachidonic acid.

What is claimed is:

1. The method for treating immunoinflammatory conditions in mammals which comprises administering to a mammal so afflicted an effective amount of a compound having the formula

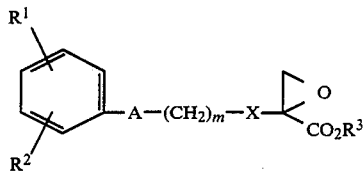

wherein

R$^1$ and R$^2$ are each, independently, hydrogen, hydroxy, lower alkyl, lower alkoxy, haloloweralkyl, halo or nitro;

R$^3$ is hydrogen, lower alkyl, or aryl of 6–10 carbon atoms;

X is

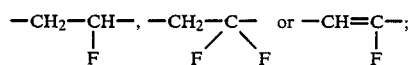

A is —CH$_2$—, —O— or —S—;

m is 1–8;

or a pharmacologically acceptable salt thereof.

2. The method of claim 1 wherein the compound has the name 2-(1-fluoro-5-phenylpentyl)-2-oxiranecarboxylic acid methyl ester.

3. The method of claim 1 wherein the compound has the name 2-[5-(4-chlorophenoxy)-1-fluoropentyl]-2-oxiranecarboxylic acid methyl ester.

4. The method of claim 1 wherein the compound has the name 2-[6-(4-chlorophenoxy)-1-fluorohexyl]-2-oxiranecarboxylic acid methyl ester.

5. The method of claim 1 wherein the compound has the name 2-[5-(4-chlorophenoxy)-1,1-difluoropentyl]-2-oxiranecarboxylic acid methyl ester.

6. The method of claim 1 wherein the compound has the name 2-[5-(4-chlorophenoxy)-1-fluoro-1-pentenyl]-2-oxiranecarboxylic acid methyl ester.

7. The method of claim 1 wherein the compound has the name 2-[6-(4-chlorophenoxy)-1,1-difluorohexyl]-2-oxiranecarboxylic acid methyl ester.

8. The method of claim 1 wherein the compound has the name 2-[5-(4-chlorophenyl)pentyl]-2-oxiranecarboxylic acid ethyl ester.

9. The method of claim 1 wherein the compound has the name 2-[6-(4-chlorophenoxy)hexyl]-2-oxiranecarboxylic acid ethyl ester.

* * * * *